US 7,247,135 B2

(12) United States Patent
Iriyama

(10) Patent No.: US 7,247,135 B2
(45) Date of Patent: Jul. 24, 2007

(54) ELECTRONIC ENDOSCOPE APPARATUS INCLUDING BRIGHTNESS ADJUSTER

(75) Inventor: Kenichi Iriyama, Saitama (JP)

(73) Assignee: PENTAX Corporation, Tokyo (JP)

( * ) Notice: Subject to any disclaimer, the term of this patent is extended or adjusted under 35 U.S.C. 154(b) by 253 days.

(21) Appl. No.: 10/882,307

(22) Filed: Jul. 2, 2004

(65) Prior Publication Data

US 2005/0010083 A1    Jan. 13, 2005

(30) Foreign Application Priority Data

Jul. 7, 2003   (JP) ............................ P2003-193056

(51) Int. Cl.
*A61B 1/06* (2006.01)
*A61B 1/04* (2006.01)
(52) U.S. Cl. .................... 600/181; 348/68; 600/178
(58) Field of Classification Search ................ 600/178, 600/180, 181; 348/68, 69
See application file for complete search history.

(56) References Cited

U.S. PATENT DOCUMENTS

| 6,724,418 | B1  | 4/2004  | Takahashi |         |
|-----------|-----|---------|-----------|---------|
| 2001/0029318 | A1* | 10/2001 | Honda et al. | 600/180 |
| 2003/0153986 | A1* | 8/2003  | Salsbury et al. | 700/11 |

FOREIGN PATENT DOCUMENTS

| JP | 6-54244    | 2/1994  |
|----|------------|---------|
| JP | 6-350903   | 12/1994 |
| JP | 2001-193896 | 7/2000  |

* cited by examiner

*Primary Examiner*—Linda C. M. Dvorak
*Assistant Examiner*—Philip R Smith
(74) *Attorney, Agent, or Firm*—Greenblum & Bernstein, P.L.C.

(57) ABSTRACT

An electronic endoscope apparatus has a light source, a luminance calculator, a controller, and a brightness adjuster. The light source illuminates an object. The luminance calculator calculates a luminance level indicating a brightness of an object image on the basis of image-pixel signals corresponding to the object image. The controller calculates and outputs a manipulated value in accordance with a luminance-difference between the luminance level and a reference luminance level indicating a standard brightness of the object image. The controller sets a non-sensitive band including a standard point corresponding to the reference luminance level. The brightness adjuster adjusts the brightness of the object image in accordance with the manipulated value. When the manipulated value is inside the non-sensitive band, the controller outputs a non-activating manipulated value so as not to activate the brightness adjuster.

9 Claims, 5 Drawing Sheets

ELECTRONIC ENDOSCOPE APPARATUS INCLUDING BRIGHTNESS ADJUSTER

BACKGROUND OF THE INVENTION

1. Field of the Invention

The present invention relates to an electronic endoscope apparatus having a video-scope with an image sensor. Especially, it relates to adjusting a brightness of an object image.

2. Description of the Related Art

In the electronic endoscope apparatus, an automatic brightness adjustment process is performed to maintain a proper brightness of an object image, which is displayed on a monitor. For example, an average luminance level of the object image, and a luminance-difference between the average luminance level and a reference luminance level indicating a proper brightness are calculated. Then, a diaphragm is opened or closed on the basis of the luminance-difference.

When using forceps, or supplying water for washing a lens and an observed portion, a minute luminance-change occurs. Also, while observing, the luminance level minutely changes due to the pulsatory motion. Since the brightness adjustment process responds to the fine luminance-change, the brightness on the monitor continuously changes in accordance with the motion of the diaphragm, which results in difficulty of viewing the observed portion.

SUMMARY OF THE INVENTION

An object of the present invention is to provide an apparatus that properly adjusts the brightness of an object image for a minute luminance change.

An electronic endoscope apparatus according to the present invention has a video-scope with an image sensor and a video-processor. The electronic endoscope apparatus has a light source, a luminance calculator, a controller, and a brightness adjuster. The light source that illuminates an object, thus an object image is formed on the image sensor, and image-pixel signals are generated in the image sensor. The luminance calculator calculates a luminance level indicating a brightness of an object image, on the basis of the image-pixel signals. The controller calculates and outputs a manipulated value in accordance with a luminance-difference between the luminance level and a reference luminance level indicating a standard brightness of the object image. For example, the controller is constructed of a digital logic circuit, also, the controller is constructed of an analog circuit with a gain compensator.

The controller sets a non-sensitive band including a standard point corresponding to the reference luminance level. In the case of a manipulated value in the non-sensitive band, a brightness of the object image is close to a brightness corresponding to the reference luminance level. The brightness adjuster adjusts the brightness of the object image in accordance with the manipulated value. For example, the brightness adjuster has a diaphragm that adjusts a light-amount of the light illuminating the object, and an actuator that drives the diaphragm.

When the manipulated value is inside the non-sensitive band, the controller outputs a non-activating manipulated value so as not to activate the brightness adjuster. When the brightness-change of the object image is relatively minute with respect to the standard brightness, the brightness adjuster does not adjust the brightness. Consequently, steady observation is continued while manipulating the video-scope.

To properly and rapidly adjust the brightness, for example, the controller sets the non-sensitive band so as to correspond to a range that is equal to or less than 10% of the total luminance levels. To raise and lower the brightness evenly, for example, the controller sets the non-sensitive band so as to be symmetric with respect to the standard point. When the manipulated value is outside the non-sensitive band, to change the brightness smoothly, the controller offsets the manipulated value so as to lower the absolute value of the manipulated value. For example, the controller offsets the manipulated value along a first direction that increases the brightness and a second direction that decreases the brightness by a half of the width of the non-sensitive band.

To set a proper non-sensitive band, the electronic endoscope apparatus has a width changing processor that changes the width of the non-sensitive band. For example, the controller detects the width of the non-sensitive band corresponding to the video-scope when the video-scope is connected to the video-processor, and sets the detected non-sensitive band.

BRIEF DESCRIPTION OF THE DRAWINGS

The present invention will be better understood from the description of the preferred embodiment of the invention set fourth below together with the accompanying drawings, in which.

DESCRIPTION OF THE PREFERRED EMBODIMENTS

Hereinafter, the preferred embodiments of the present invention are described with reference to the attached drawings.

Figure 1:
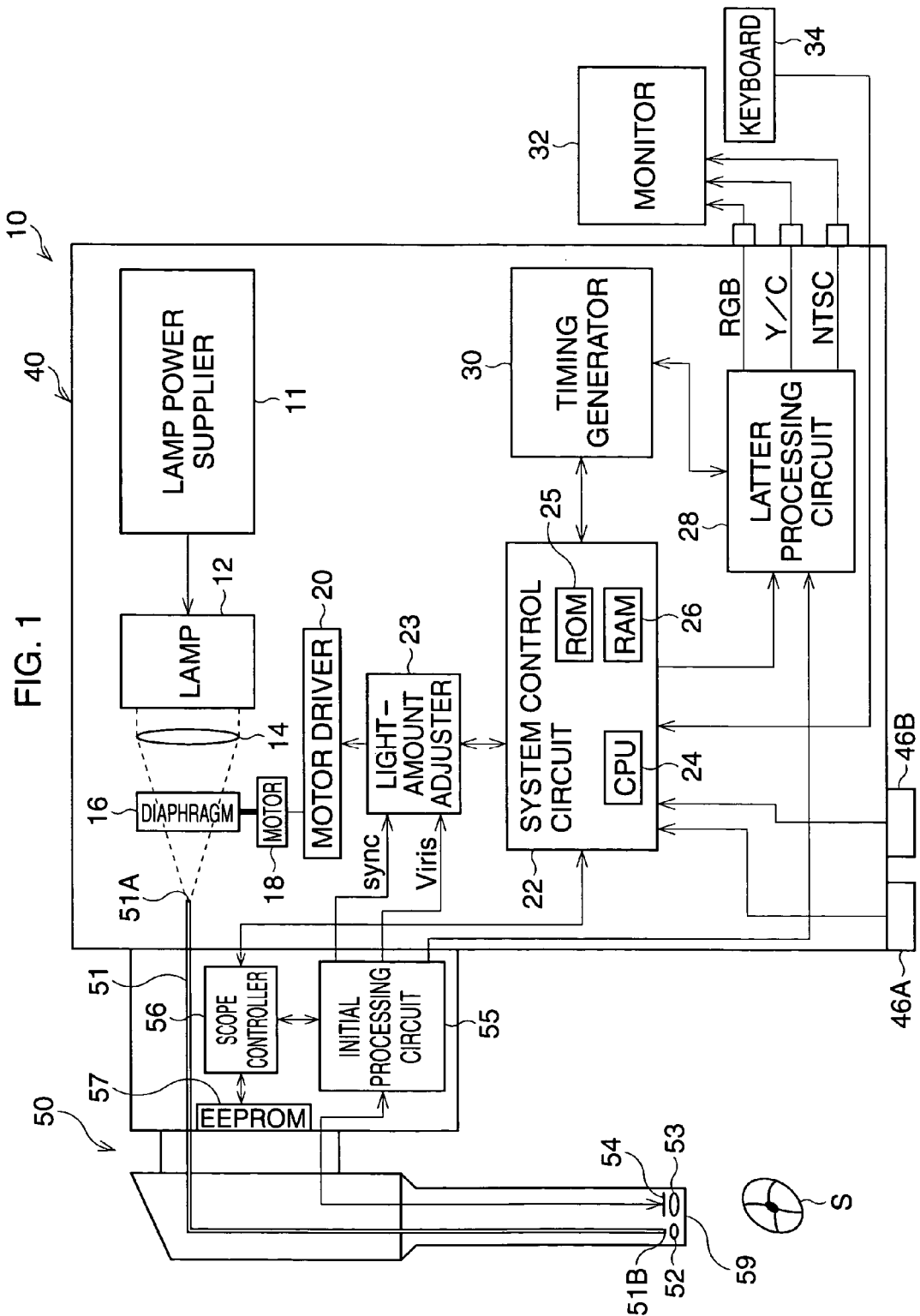
FIG. 1 is a block diagram of an electronic endoscope apparatus according to a first embodiment.

FIG. 1 is a block diagram of an electronic endoscope apparatus according to a first embodiment.

An electronic endoscope apparatus 10 has a video-scope 50 with a CCD 54, and a video-processor 40. The video-scope 50 is detachably connected to the video-processor 40, and further a TV monitor 32 and a keyboard 34 are connected to the video-processor 40.

When a lamp switch (not shown) is turned ON, electric power is supplied from a lamp power supplier 11 to a lamp 12, so that light is emitted from the lamp 12 and is directed toward an incident surface 51A of a fiber-optic bundle 51 via a collecting lens 14 and a diaphragm 16. The fiber-optic bundle 51, provided in the video-scope 50, directs the light toward the tip portion 59 of the video-scope 50. The light passing through the fiber-optic bundle 51 exits from the end surface 51B of the fiber-optic bundle 51 and is emitted toward an object S via a diffusion lens 52, so that the object S is illuminated.

The light reflected on the object S passes through an objective lens 53 and reaches the CCD 54, so that an object image is formed on a photo-sensor area of the CCD 54. For the color image process, herein, an on-chip color filter method using a one-chip color filter is applied. A color filter (not shown), checkered by four color elements of Yellow (Ye), Magenta (Mg), Cyan (Cy), and Green (G), is arranged on the photo-sensor area such that the four color elements are opposite to the pixels arranged in the photo-sensor area. Analog image-pixel signals, corresponding to the light passing through the color filter, are generated in the CCD 54 by the photoelectric transform effect. The generated color image-pixel signals are composed of plural color signal components. Then, one field worth of image-pixel signals is read from the CCD 54 at regular time intervals in accordance with the so called "color difference line sequential system". Herein, the NTSC standard is used as the color TV standard, accordingly, one field worth of image-pixel signals is read from the CCD 54 at 1/60 second time intervals, and then is fed to an initial processing circuit 55.

In the initial processing circuit 55, various processes, such as a white balance process, gamma correction, and so on, are performed for the image-pixel signals, which are then converted to digital image signals. The digital image signals are temporarily stored in a frame memory in the initial processing circuit 55 and are then fed to a latter processing circuit 28 in the video-processor 40.

Further, one field worth of luminance signals "Viris" are successively obtained from the image-pixels in the initial processing circuit 55, and are fed to a light-amount adjuster 23 in the video-processor 40 at 1/60-second intervals, in accordance with the NTSC standard.

In the latter processing circuit 28, a given process is performed for the digital image signals, and the digital image signals are converted to video signals, such as RGB component signals. The video signals are fed to the monitor 32, thus the object image is displayed on the monitor 32.

The system control circuit 22 including a CPU 24, a ROM 25, and a RAM 26 controls the video-processor 40, and feeds control signals to the light-amount adjuster 23, the latter processing circuit 28, and so on. The timing generator 30 outputs clock pulses for adjusting a signal-process timing to each circuit, and feeds synchronized signals, which accompany the video signals, to the latter processing circuit 28.

In the video-scope 50, a scope controller 56 and an EEPROM 57 are provided. The scope-controller 56 controls the video-scope 50, whereas data associated with the video-scope 50, especially, a light-amount adjustment process is stored in the EEPROM 57. The scope controller 56 reads the data from the EEPROM 57, and outputs control signals to the initial processing circuit 55. When the video-scope 50 is connected to the video-processor 40, the data is transmitted between the scope-controller 56 of the video-scope 50 and the system control circuit 22 of the video-processor 10.

The diaphragm 16, provided between the incident surface 51A of the fiber-optic bundle 51 and the collecting lens 16, is driven for adjusting the amount of light illuminating the object S. The light-amount adjuster 23, which is constructed of a DSP (Digital Signal Processor), controls the driving of the diaphragm 16 so as to maintain the proper brightness of the object image. Namely, the light-amount adjuster 23 calculates a manipulated value for the diaphragm 16, and outputs a control signal to a motor driver 20. The motor driver 20 outputs a driving signal to a stepping motor 18 so that the diaphragm 16 opens/closes by a given amount in accordance with the manipulated value. The light-amount adjuster 23 successively outputs the manipulated value in accordance with the luminance signals, which is input to the light-amount adjuster 23.

A switch 46A for setting a reference luminance level, which indicates a standard luminance level with respect to the light-amount adjustment process, is provided on the video-processor 40. The switch 46A is operated when changing the reference luminance level. A predetermined reference luminance level is temporarily stored in the RAM 26 as data. The data is fed to the light-amount adjuster 23. A metering selecting switch 46B is a switch for setting the metering to a "peak metering" or an "average metering". As for the gamma correction, the gamma in the characteristic curve (tone curve) is changeable by operating the keyboard 34.

Figure 2:
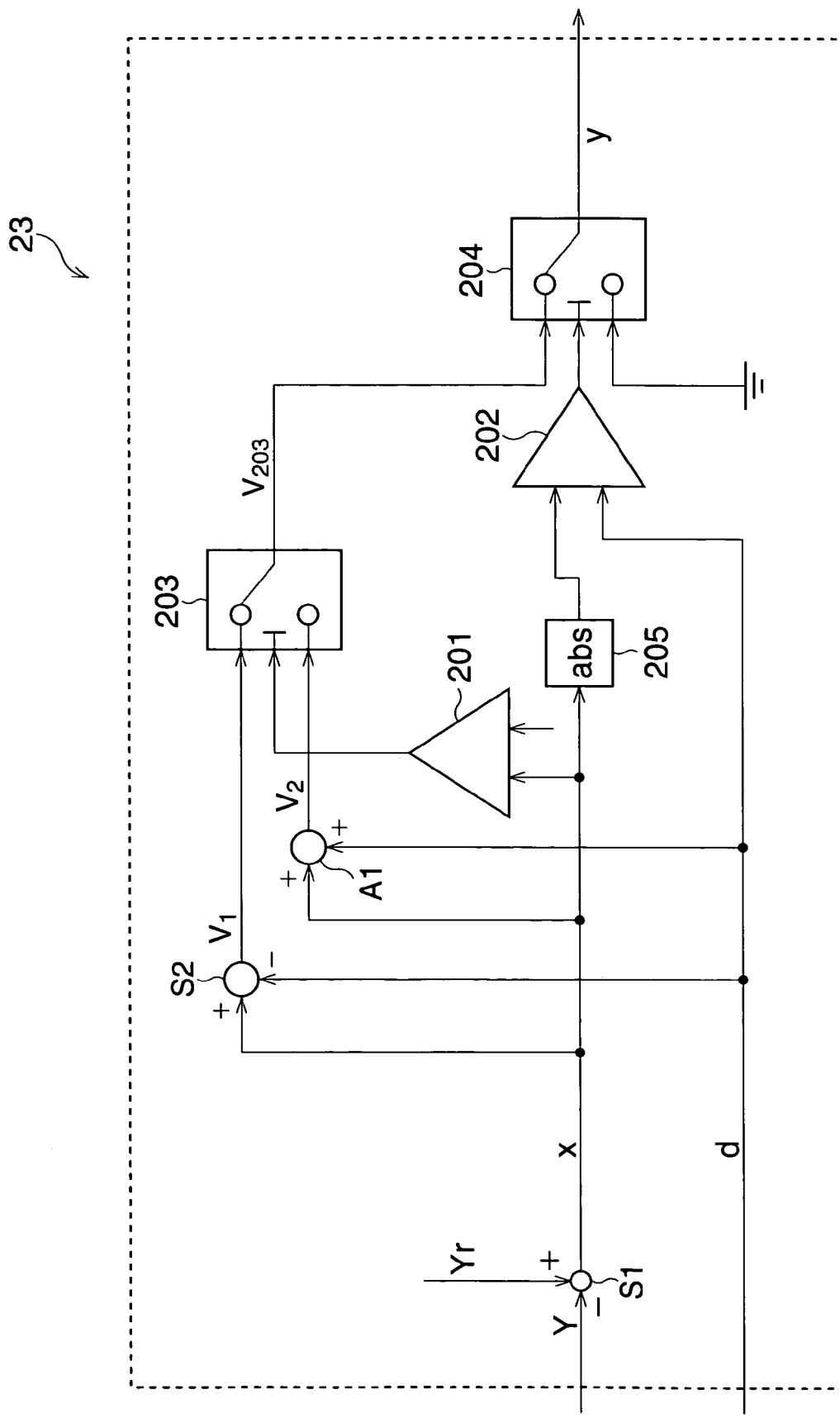
FIG. 2 is a view showing an electric circuit of a light-amount adjuster.

FIG. 2 is a schematic view showing an electric circuit of the light-amount adjuster 23.

The light-amount adjuster 23 has comparators 201 and 202, selecting switches 203 and 204, an absolute operator 205, subtracters S1 and S2, and an adder A1. The comparator 201 is connected to the switch 203, whereas the comparator 202 is connected to the switch 204. The absolute operator 205 is connected to the comparator 202.

In the light-amount adjuster 23, a representative luminance level "Y", corresponding to one field object image, is calculated on the basis of one field worth of luminance signals "Viris", which is fed from the initial processing circuit 55. For example, in the case of the average metering, an average luminance level is calculated. Then, the luminance-difference is calculated by subtracting the luminance level "Y" from the reference luminance level "Yr", which is predetermined by the luminance level switch 46A. Herein, the brightness of the object image is represented by 256 levels, and the magnitude of a luminance level is represented by an integer from "0" to "255". The reference luminance level "Yr" is initially set to a middle luminance level, "128". The luminance-difference is fed to the comparator 201, the absolute operator 205, the subtracter S2, and the adder A1, as an input manipulated value "x".

In addition to the input manipulated value "x", a threshold value "d (>0)" is input to the comparator 202, the subtracter S2, and the adder A1. The threshold value "d" corresponds a length or width of a non-sensitive band "D" wherein the diaphragm 16 is not driven, as described later. The threshold value "d" is stored in the EEPROM 57 in the video-scope 50. When the video-scope 50 is connected to the video-processor 40, data associated with the threshold value "d" is read from the EEPROM 57, and the threshold value "d" is preset in the light-amount adjuster 23 before manipulating the video-scope 50.

At the subtracter S2, the threshold value "d" is subtracted from the input manipulated value "x". The subtracted manipulated value "$V_1(=x-d)$" is input to the switch 203. On the other hand, at the adder A1, the input manipulated value "x" is added to the threshold value "d", and the added input manipulated value "$V_2 (=x+d)$" is input to the switch 203.

The comparator 201 compares the input manipulated value "x" with Zero, namely, it determines whether the input manipulated value "x" is equal to or is more than Zero level. When the input manipulated value "x" is equal to or is more than Zero, the comparator 201 controls the switch 203 so as to output the subtracted manipulated value "$V_1$," from the switch 203. On the other hand, when the input manipulated value "x" is less than Zero, the comparator 201 controls the switch 203 so as to output the added input manipulated value "$V_2$" from the switch 203. Accordingly, an output value "$V_{203}$" from the switch 203 is represented as following formulae:

$$V_{203}=V_1=x-d(x\geq 0) \quad (1)$$

$$V_{203}=V_2=x+d(x<0) \quad (2)$$

The output value "$V_{203}$" is input to the switch 204.

In the absolute operator 205, the absolute value of the input manipulated value "|x|" is obtained and is fed to the comparator 202. The comparator 202 compares the absolute value of the input manipulated value "|x|" with the threshold value "d", namely, compares whether the absolute of the input manipulated value "|x|" is equal to or more than the threshold value "d". The switch 204 selectively outputs one of the output value "$V_{203}$", fed from the switch 203, and the value Zero, as an output manipulated value "y", in accordance with a control signal fed from the comparator 202. When the absolute value of the input manipulated value "|x|" is equal to or more than the threshold value "d", the comparator 202 outputs a control signal to the switch 204 so as to output the output value "$V_{203}$" from the switch 204. On the other hand, when the absolute value of the input manipulated value "|x|" is less than the threshold value "d", the comparator 202 output a control signal to the switch 204 so as to outputs the value Zero. Accordingly, the output manipulated value "y", which is output from the switch 204, is represented by the following formulae:

$$y=V_{203}(|x|\geq d) \quad (3)$$

$$y=0 \ (|x|<d) \quad (4)$$

The output manipulated value "y" is multiplied by a gain coefficient in an amplifier (not shown) so that a manipulated value corresponding to an actual open/close-amount of the motor 18 is obtained, and is fed to the motor driver 20.

Figure 3:
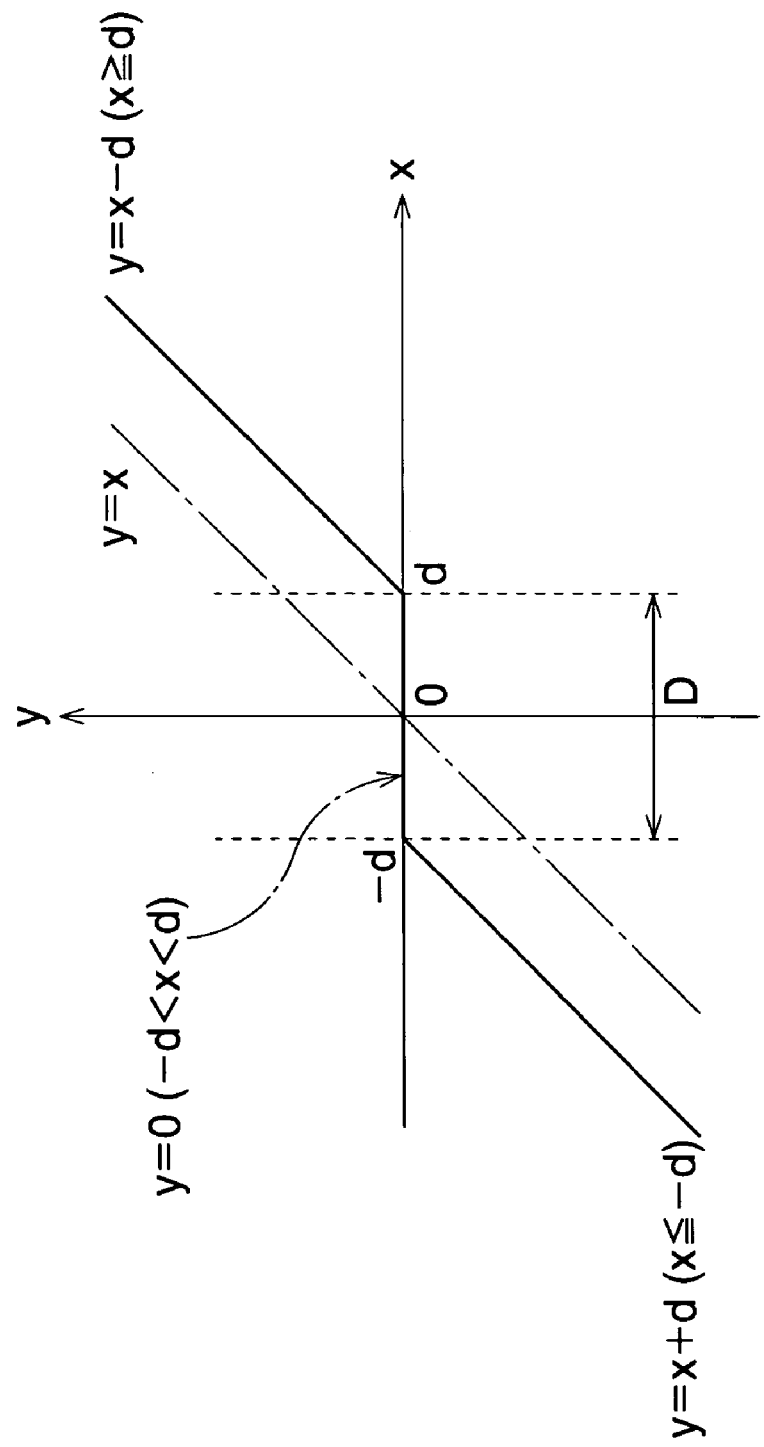
FIG. 3 is a view showing a graph, which represents a relationship between an input manipulated value and an output manipulated value.

FIG. 3 is a view showing a graph, which represents a relationship between the input manipulated value "x" and the output manipulated value "y". Herein, the vertical-axis is the output manipulated value "y", whereas the horizontal-axis is the input manipulated value "x".

As shown in FIG. 3, the origin is defined as a point where the luminance level difference "Yr-Y" is Zero. The non-sensitive band "D" is defined as the range from "-d" to "d" such that the center of the band "D" is positioned at the origin. As can be seen from the formula (4), the output manipulated value "y" is Zero when the input manipulated value "x" is in the non-sensitive band "D". Consequently, the stepping motor 18 is not driven.

Herein, the width of the non-sensitive band "2d" is set to about 10% of the total (=256) luminance levels. Namely, the non-sensitive band "D" is positioned in a range from "118 to 138" of the luminance levels corresponding to the input manipulated values "x". A luminance-change in the non-sensitive band "D" does not substantially affect the observation of the object image. In other words, the luminance level "Y" included in the non-sensitive band "D" can be substantially regarded as the reference luminance level "Yr".

The length of the non-sensitive band "2d" is changeable by operating the keyboard 34. When the keyboard 34 is operated to set the non-sensitive band "D", a signal representing the determined non-sensitive band "D" is fed to the light-amount adjuster 23. The proper width of the non-sensitive band "2d", namely, the threshold value "d" varies with the characteristics of the diaphragm 16, the CCD 54, the gamma correction, and so on. For example, the length of the non-sensitive band "2d" is set in accordance with the sensitivity of the CCD 54, or the dynamic range of the CCD 54. The width of the non-sensitive band "2d" is set such that the percentage is equal to or less than 10%.

Also, the width of the non-sensitive band "2d" is defined in accordance with the characteristic curve associated with the gamma correction. When the curve is sharp in the middle luminance level, the threshold value "d" is set to a relatively small value. On the other hand, when the curve is gentle in the middle luminance level, the threshold value "d" is set to a relatively large value.

When the input manipulated value "x" is outside the non-sensitive band "D", namely, the absolute value of the input manipulated value "|x|" exceeds the threshold value "d", the output manipulated value "y" is defined in accordance with formulae (1) and (2). When the input manipulated value "x" is negative, namely, the detected luminance level "Y" is larger than the reference luminance level "Yr", the output manipulated value "y" is calculated using formula (2). Thus, the driving signal is fed from the motor driver 20 to the motor 18 so as to close the diaphragm 16. On the other hand, when the input manipulated value "x" is positive, namely, the detected luminance level "Y" is smaller than the reference luminance level "Yr", the output manipulated value "y" is obtained using formula (1). Thus, the driving signal is fed from the motor driver 20 to the motor 18 so as to open the diaphragm 16.

Note that, as described above, the output manipulated value "y" is multiplied and the actual manipulated value is output to the motor driver 20. However, the actual manipulated value has a linear relationship with respect to the output manipulated value "y", therefore, the actual manipulated value is represented by the function shown in FIG. 3 and the formulae (1) and (2).

Figure 4:
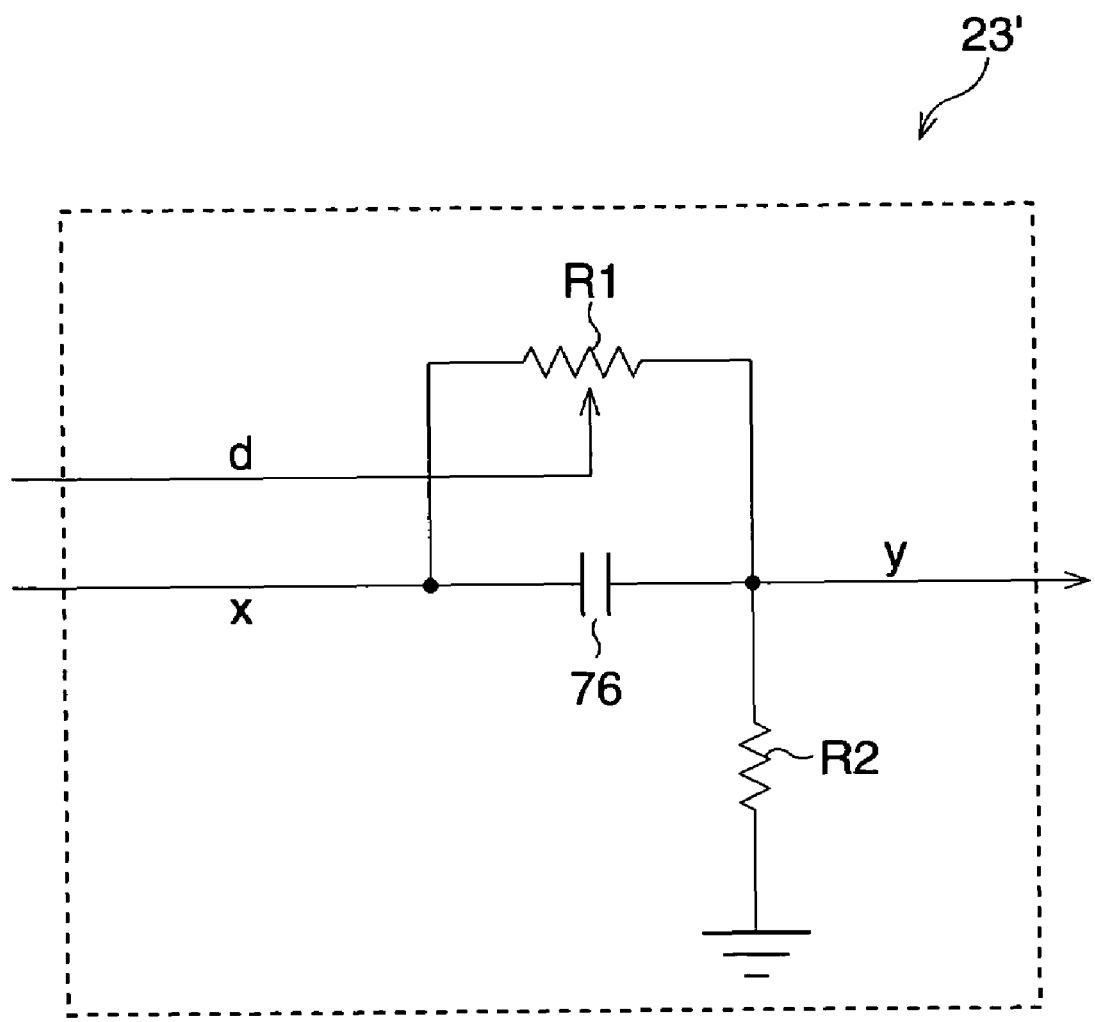
FIG. 4 is a view showing an electric circuit of a light-amount adjuster according to a second embodiment.
Figure 5:
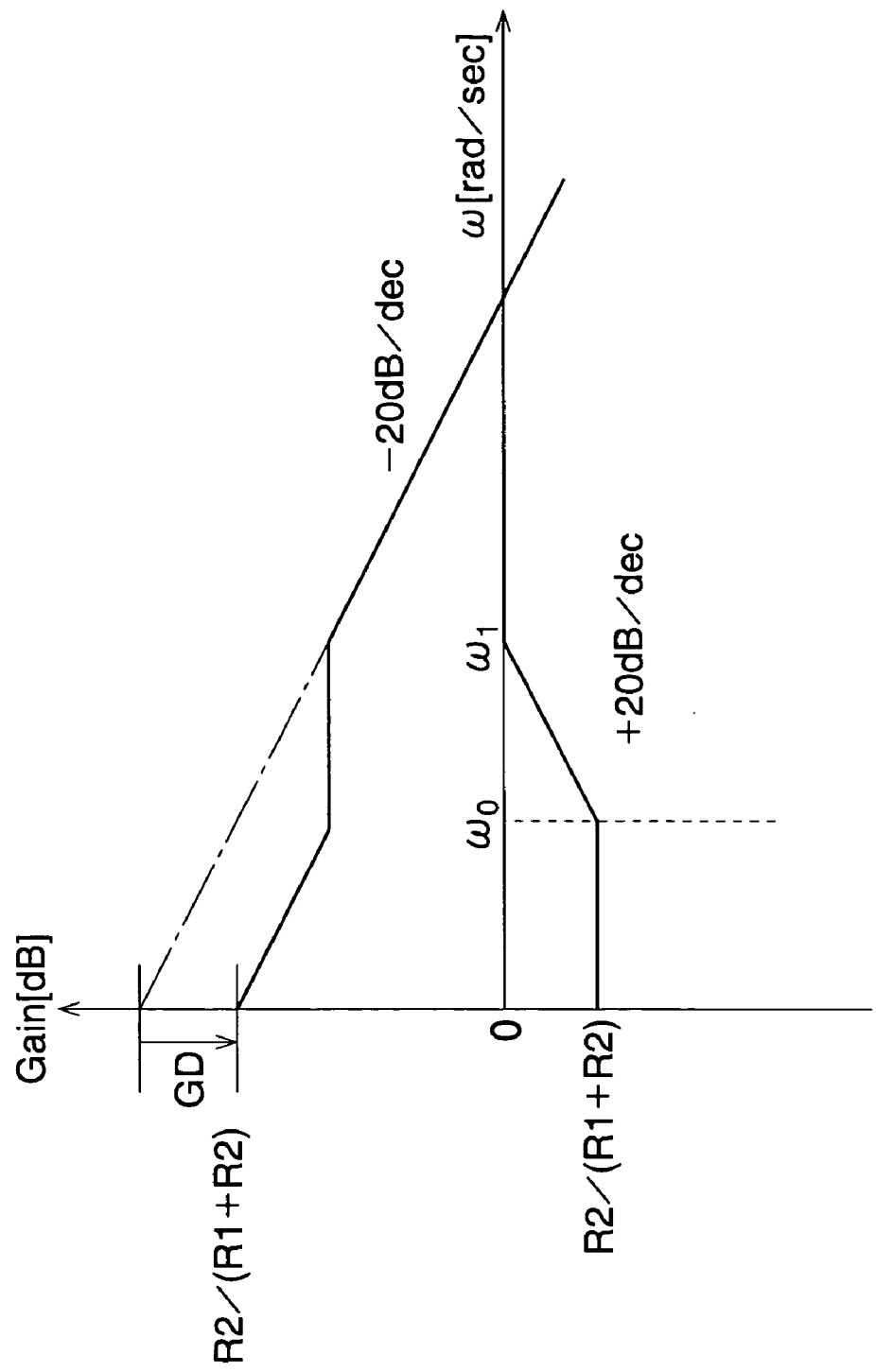
FIG. 5 is a bode diagram indicating the open loop gain characteristics.

With reference to FIGS. 4 and 5, an electronic endoscope apparatus according to a second embodiment is explained. The second embodiment is different from the first embodiment in that the light-amount adjuster 23 is constructed of an analog circuit.

FIG. 4 is a view schematically showing an electric circuit of a light-amount adjuster.

A light-amount adjuster 23' is a gain compensator performing as a part of a closed loop control, and has a variable resistor R1, a fixed resistor R2, and a capacitor 76. When an input manipulated value "x" is input to the light-amount adjuster as an analog signal, the input manipulated value "x" is corrected so as to decrease the absolute value of the input manipulated value "|x|". An output manipulated value "y" is output from the light-amount adjuster 23. The value of the variable resistor 72 sets the width of the non-sensitive range "2d". The length "2d" varies with the value of the resistor 72.

FIG. 5 is a bode diagram indicating the open loop gain characteristics. Herein, the vertical-axis indicates the gain for the electric circuit of the light-amount adjuster 23', whereas the horizontal-axis indicates the frequency.

As shown in FIG. 5, the lowering of the gain occurs in a low frequency range. The magnitude of the gain lowering "GD" in the low frequency range is given by the following formula:

$$GD=R2/(R1+R2) \quad (5)$$

The magnitude of the gain lowering "GD" is constant in the range from 0 to $\omega_0$, namely, the magnitude of the gain lowering "GD" is obtained by the formula (5). Then, the magnitude of the gain lowering "GD" decreases gradually in the range from $\omega_0$ to $\omega_1$, in accordance with a straight line having a slope of "+20 db/dec". When the frequency exceeds $\omega_1$, the magnitude of the gain lowering "GD" becomes Zero, and the gain characteristic is represented by a straight line having a slope of "-20 db/dec". As the gain decreases in the low frequency range, the light-amount adjuster 23' functions in the same way as in the first embodiment.

The brightness of the object image may be controlled by another methods (for example, using an electronic shutter function) in place of the light-amount adjustment using the diaphragm.

The diaphragm 16 may be driven when the manipulated value exceeds the threshold value. Namely, the following formulae may be used in place of formula (3) and (4).

$$y = V_{203} (|x| > d) \tag{6}$$

$$y = 0 (|x| \leq d) \tag{7}$$

Finally, it will be understood by those skilled in the art that the foregoing description is of preferred embodiments of the device, and that various changes and modifications may be made to the present invention without departing from the spirit and scope thereof.

The present disclosure relates to subject matters contained in Japanese Patent Application No.2003-193056 (filed on Jul. 7, 2003), which is expressly incorporated herein, by reference, in its entirety.

The invention claimed is:

1. An electronic endoscope apparatus having a video-scope with an image sensor and a video-processor, comprising:
   a light source that illuminates an object, an object image being formed on the image sensor, image-pixel signals being generated by the image sensor;
   a luminance calculator that calculates a luminance level indicating a brightness of an object image on the basis of the image-pixel signals;
   a controller that calculates and outputs a manipulated value in accordance with a luminance-difference between the luminance level and a reference luminance level indicating a standard brightness of the object image, said controller setting a non-sensitive band including a standard point corresponding to the reference luminance level; and
   a brightness adjuster that adjusts the brightness of the object image in accordance with the manipulated value, said controller outputting a non-activating manipulated value so as not to activate said brightness adjuster when the manipulated value is inside the non-sensitive band;
   wherein the controller offsets the manipulated value so as to lower the absolute value of the manipulated value when the manipulated value is outside the non-sensitive band along a first direction that increases the brightness and a second direction that decreases the brightness by a half of a width of the non-sensitive band, the controller offsetting the manipulated value so as to maintain a linear relationship between the manipulated value and the luminance difference.

2. The electronic endoscope apparatus of claim 1, wherein the controller sets the non-sensitive band so as to be symmetric with respect to the standard point.

3. The electronic endoscope apparatus of claim 1, wherein said controller comprises a digital logic circuit.

4. The electronic endoscope apparatus of claim 1, wherein said controller comprises an analog circuit, and said analog circuit comprises a gain compensator.

5. The electronic endoscope apparatus of claim 1, further comprising a width changing processor that changes a width of the non-sensitive band.

6. The electronic endoscope apparatus of claim 1, wherein said brightness adjuster comprises:
   a diaphragm that adjusts an amount of light illuminating the object; and
   an actuator that drives said diaphragm.

7. The electronic endoscope apparatus of claim 1, wherein said controller detects a width of the non-sensitive band corresponding to the video-scope when the video-scope is connected to the video-processor, and sets the width of the non-sensitive band corresponding to the connected video-scope.

8. An apparatus for adjusting the brightness of an object image, said apparatus being incorporated in an electronic endoscope apparatus, the apparatus for adjusting comprising:
   a luminance calculator that calculates a luminance level indicating a brightness of an object image, on the basis of image-pixel signals corresponding to the object image;
   a controller that calculates and outputs a manipulated value in accordance with a luminance-difference between the luminance level and a reference luminance level indicating a standard brightness of the object image, said controller setting a non-sensitive band including a standard point corresponding to the reference luminance level; and
   a brightness adjuster that adjusts the brightness of the object image in accordance with the manipulated value, said controller outputting a non-activating manipulated value so as not to activate said brightness adjuster when the manipulated value is inside the non-sensitive band;
   wherein the controller offsets the manipulated value so as to lower the absolute value of the manipulated value when the manipulated value is outside the non-sensitive band along a first direction that increases the brightness and a second direction that decreases the brightness by a half of a width of the non-sensitive band, the controller offsetting the manipulated value so as to maintain a linear relationship between the manipulated value and the luminance difference.

9. A method for adjusting a brightness of an object image that is observed by using an electronic endoscope, comprising:
   calculating a luminance level indicating a brightness of an object image on the basis of image-pixel signals, which are read from an image sensor provided in a video-scope;
   calculating a manipulated value in accordance with a luminance-difference between the luminance level and a reference luminance level indicating a standard brightness of the object image;
   setting a non-sensitive band including a standard point corresponding to the reference luminance level;
   adjusting the brightness of the object image in accordance with the manipulated value; and
   outputting a non-activating manipulated value so as not to activate said brightness adjuster when the manipulated value is inside the non-sensitive band;
   wherein setting the non-sensitive band comprises offsetting the manipulated value so as to lower the absolute value of the manipulated value when the manipulated value is outside the non-sensitive band along a first direction that increases the brightness and a second direction that decreases the brightness by a half of a width of the non-sensitive band, the offsetting being arranged so as to maintain a linear relationship between the manipulated value and the luminance difference.

* * * * *